United States Patent
Matsuda et al.

(10) Patent No.: US 6,461,842 B1
(45) Date of Patent: Oct. 8, 2002

(54) PROCESS FOR PRODUCING COENZYME $Q_{10}$

(75) Inventors: Hideyuki Matsuda; Makoto Kawamukai, both of Shimane-ken; Kazuyoshi Yajima; Yasuhiro Ikenaka, both of Hyogo-ken; Kenichi Nishi, Kyoto-fu; Junzo Hasegawa; Satomi Takahashi, both of Hyogo-ken, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/673,018

(22) PCT Filed: Feb. 3, 2000

(86) PCT No.: PCT/JP00/00588

§ 371 (c)(1),
(2), (4) Date: Oct. 10, 2000

(87) PCT Pub. No.: WO00/47746

PCT Pub. Date: Aug. 17, 2000

(30) Foreign Application Priority Data

Feb. 10, 1999 (JP) .............................................. 11-32657

(51) Int. Cl.[7] .................................................. C12N 9/10
(52) U.S. Cl. ...................... 435/193; 435/41; 435/69.1; 435/252.33; 435/320.1; 536/23.2; 536/23.6
(58) Field of Search .......................... 435/41, 69.1, 193, 435/252.33, 320.1; 536/23.2, 23.6

(56) References Cited

U.S. PATENT DOCUMENTS 6,103,488 A * 8/2000 Matsuda et al. ............... 435/41

FOREIGN PATENT DOCUMENTS

| JP | 10-057072 | 3/1998 |
|----|-----------|--------|
| JP | 11-056372 | 3/1999 |
| JP | 11-178590 | 7/1999 |

OTHER PUBLICATIONS

H. Matsuda et al., "Molecular colning and mutational analysis of the ddsA gene encoding decaprenyl disphosphate synthase from Gluconobacter suboxydans", Eur. J. Biochem., (1998), vol. 225, No. 1, pp. 52–59.

M. Kawamukai et al., "Analysis of the decaprenyl disphosphate synthase (dps) gene in fission yeast suggests a role of ubiquinone as an antioxidant", J. Biochem., (1997), vol. 121, No. 3, pp. 496–505.

Kawamukai M. Accession AB006850. Aug. 11, 1998 (Alignment No. 1).*

Kawamukai M. Accession AB006850. Aug. 11, 1998 (Alignment No. 2).*

Okada et al. Molecular cloning and mutational analysis of the ddsA gene encoding decaprenyl disphosphate synthase from Gluconobacter suboxydans. Eur J Biochem Jul. 1, 1998;255(1):52–9.*

* cited by examiner

Primary Examiner—Ponnathapu Achutamurthy
Assistant Examiner—Christian L. Fronda
(74) Attorney, Agent, or Firm—Wenderoth, Lind & Ponack, L.L.P.

(57) ABSTRACT

A gene of decaprenyl diphosphate synthase, which is the key gene participating in the biosynthesis of coenzyme $Q_{10}$ was isolated from a bacterium belonging to the family Rhizobiaceae. By transferring this gene into a microorganism such as *Escherichia coli* and expressing therein, coenzyme $Q_{10}$ can be effectively produced.

16 Claims, 2 Drawing Sheets

PROCESS FOR PRODUCING COENZYME Q₁₀

This is a 371 application of international application No. PCT/JP00/00588 filed Feb. 3, 2000.

This application is a 371 application of International PCT Application No. PCT/JP00/00588, filed Feb. 3, 2000, currently pending, which claims priority under 35 USC 119 of Japanese Patent Application No. 32657, filed Feb. 10, 1999, the disclosure of both applications are fully incorporated herein by reference.

BACKGROUND OF THE INVENTION

1. Field of the Invention

The present invention relates to a process for producing coenzyme $Q_{10}$, which can be used as a pharmaceutical agent and the like. In more detail, the present invention relates to a process for producing coenzyme $Q_{10}$ by isolating a gene coding for an enzyme responsible for biosynthesizing coenzyme $Q_{10}$ side chain, the key enzyme in the coenzyme $Q_{10}$ biosynthetic pathway, i.e. decaprenyl diphosphate synthase, from a bacterium belonging to the family Rhizobiaceae, and transferring said gene into a microorganism to produce coenzyme $Q_{10}$.

2. Description of the Related Art

Industrially, coenzyme $Q_{10}$ has been produced by isolating a coenzyme from plants such as tobacco and synthetically altering the side chain.

In addition, it has been known that coenzyme $Q_{10}$ is produced by a wide variety of organisms including from microorganisms such as bacterium and yeast, to higher plants and animals. One of the most effective processes for producing coenzyme $Q_{10}$ is believed to be a process which comprises culturing the microorganism and extracting the compound from the culture. Said process has also been used in industrial production of coenzyme $Q_{10}$. However, the above known processes do not provide enough productivity because of their low yield or complicated operation.

Though there are some differences between the prokaryotic and eucaryotic pathways for biosynthesis of coenzyme $Q_{10}$, both pathways consist of complicated multi-step reactions in which many enzymes are involved. They basically consist of the following three steps; synthesizing decaprenyl diphosphate, which is used for the prenyl side chain of coenzyme $Q_{10}$; synthesizing parahydroxy benzoic acid, which is used for the quinone ring; and binding those two components and converting the substituents sequentially to give coenzyme $Q_{10}$. The reaction, which determines the length of the side chain and is believed to be the rate-limiting step in the biosynthetic pathway, that is, the reaction in which decaprenyl diphosphate synthase is involved, is believed to be the most important reaction. Therefore, in order to produce coenzyme $Q_{10}$ effectively, it might be a good idea to isolate the decaprenyl diphosphate synthase gene, the key gene in the biosynthetic pathway, and to use said gene for improving productivity. One of the potential candidates for the gene sources is a bacterium belonging to the family Rhizobiaceae, which produces relatively large amounts of coenzyme $Q_{10}$.

Until now, decaprenyl phosphoric acid synthase genes had been isolated from several microorganisms including *Schizosaccaromyces pombe* (Japanese Patent Application Laid Open No. H09-173076) and *Gluconobacter suboxydans* (Japanese Patent Application Laid Open Open No. H10-57072). However, they do not show enough productivity for coenzyme $Q_{10}$ and therefore, the art had not yet achieved effective culture, isolation or purification with those microorganisms. Accordingly, it has been desired to isolate a gene of said enzyme from a microorganism having high coenzyme $Q_{10}$ producing ability.

SUMMARY OF THE INVENTION

The present invention has been made to solve the above-mentioned problem of low productivity. The object of the present invention is to provide a process for producing coenzyme $Q_{10}$ effectively by means of a microorganism, by isolating a gene coding for coenzyme $Q_{10}$-side chain synthetic enzyme from a bacterium belonging to the family Rhizobiaceae and using the gene.

According to the present invention, decaprenyl diphosphate synthase gene, the key gene in the biosynthetic pathway for coenzyme $Q_{10}$, was isolated from a bacterium belonging to the family Rhizobiaceae. An effective coenzyme $Q_{10}$ production has been achieved by transferring the gene into a microorganism such as *Escherichia-coli* and expressing therein.

The inventors have tried to isolate the gene of decaprenyl diphosphate synthase from a bacterium belonging to the family Rhizobiaceae which produces relatively large amounts of coenzyme $Q_{10}$ and succeeded in isolating said gene.

Accordingly, the present invention provide a DNA comprising a DNA sequence of the Seq. ID No. 1, or a sequence having deletion, addition or insertion of one or more base in the sequence and coding for decaprenyl diphosphate synthase. The present invention also provide a protein having an amino acid sequence of the Seq. ID No. 2, or an amino acid sequence having deletion, addition or insertion of one or more amino acid in said sequence and having decaprenyl diphosphate synthase activity; and a DNA encoding said amino acid sequence.

The present invention also provide a process for producing coenzyme $Q_{10}$ comprising the steps of transferring the above described DNA sequence into a host microorganism and culturing the microorganism. The host microorganism used in the present invention is not limited but preferably is *Escherichia coli*. Although a normal *Escherichia coli* produces coenzyme $Q_8$, according to the present invention, *Escherichia coli* can be modified to produce coenzyme $Q_{10}$.

In addition, the present invention provides an expression vector comprising the above-described DNA sequence. The expression vector of the present invention may be constructed by using any of known vector systems. For example, pQAD-1, which is constructed by transferring the gene of the Seq. ID No. 1 into the known expression vector system pUCNT, is provided.

According to the invention, a host microorganism transformed with the above-described DNA sequence is also provided. For the host microorganism in the present invention, *Escherichia coli* is preferably used.

DESCRIPTION OF THE PREFERRED EMBODIMENTS

The inventors studied intensively to isolate the desired gene from the bacterium belonging to the family Rhizobiaceae, which produces relatively high amounts of coenzyme $Q_{10}$, and succeeded in obtaining a fragment of said gene by means of PCR technique.

The inventors compared known decaprenyl diphosphate synthase genes and polyprenyl diphosphate synthase genes, analogous enzymes of the former that participate in the biosynthesis of longer prenyl chains to provide coenzyme Qs having different length side chains; and based on the homologous regions between those sequences, several PCR primers were designed. Various combinations of the obtained primers were tested to determine PCR condition. It was found that a 400 bp gene fragment of the desired enzyme was amplified from chromosomal gene of Agrobacterium sp. KNK712 (FERM BP-1900) by using DPS-1 (5'-AAGGATCCTNYTNCAYGAYGAYGT-3' (SEQ ID No. 3)) and DPS-2 (5'-AAGGATCCTCRTCNACNARYTGRAA-3' (SEQ ID No. 4)) (wherein R represents A or G, Y represents C or T, and N represents G, A, T or C) as PCR primers, carrying out the PCR process at 94° C. for 1 minute than 25 cycles of thermal cycling at 94° C. 1 min.→50° C. 1 min.→75° C. 1 min. It was confirmed by sequencing the obtained gene.

In order to obtain full length gene of said enzyme, in the next step, Agrobacterium sp. KNK 712 (FERM BP-1900) chromosomal gene was digested with EcoRI restriction enzyme and the obtained fragments were transferred into λ phage vector to provide a recombinant phage library. The plaques were blotted on a nylon filter and the filter was subjected to plaque hybridization with the labeled PCR fragment and then, a clone comprising full length of decaprenyl diphosphate synthase gene could be obtained.

Base sequence of the decaprenyl diphosphate synthase gene contained in the obtained clone was determined to give the sequence of Seq. ID No. 1. The amino acid sequence deduced from the base sequence contained regions having sequences characteristic to decaprenyl diphosphate synthase.

In order to express the decaprenyl diphosphate synthase gene, it is required to ligate said gene into a vector at a region downstream to an appropriate promoter. For example, an expression vector may be constructed by excising a DNA fragment containing desired gene by means of restriction enzyme or by amplifying the fragment coding for the enzyme by means of PCR, then transferring the fragment into a vector having a promoter. For example, an expression vector system pUCNT (described in WO94/03613) may be transfected with said gene to provide an expression vector pQAD1 for decaprenyl diphosphate synthase gene.

Then, an appropriate microorganism may be used for producing coenzyme $Q_{10}$ by transforming the same with said expression vector for the enzyme. For example, a *Escherichia coli,* which produces originally coenzyme $Q_8$, can be transformed by pQAD1, the expression vector for decaprenyl diphosphate synthase gene, to produces significantly higher amount coenzyme $Q_{10}$, which is not originally produced, than the amount of coenzyme $Q_8$ production.

The transformed *Escherichia coli, Escherichia coli* HB101 pQAD1 was deposited in the National Institute of Bioscience and Human-Technology, Agency of Industrial Science and Technology, Ministry of International Trade and Industry with the accession number of FERM BP-6538.

The gene provided by the present invention may be utilized alone or may also be co-transferred into a microorganism with another biosynthetic gene and expressed therein to give a better effect.

According to the process of the present invention for producing coenzyme $Q_{10}$, the host microorganism transformed with the gene may be cultured to produce coenzyme $Q_{10}$. The condition for the culture is not limited and may be determined depending on the selected host microorganism. Conditions for culturing various host microorganisms are well known in the art. After the culture is completed, the host microorganisms may be harvested and coenzyme $Q_{10}$ may be isolated and purified by means of an appropriate procedure. The method for isolating coenzyme Qs from the host microorganism is well known in the art.

EXAMPLES

The present invention will be described in more detail by means of the following examples. The examples are for the purpose of explanation only and do not limit the scope of the invention in any means.

Example 1

A chromosomal DNA of Agrobacterium sp. KNK712 was prepared by the method of Marmur, J. Mol. Biol. Vol. 3, pp 208–218 (1961). PCR primers were designed based on base sequence homology between the DNA and the known long chain prenyl phosphoric acid synthase gene, to give two primers DPS-1 (5'-AAGGATCCTNYTNCAYGAYGAYGT-3' (SEQ ID No. 3)) and DPS-2 (5'-AAGGATCCTCRTCNACNARYTGRAA-3' (SEQ ID No. 4)). Wherein, R represents A or G, Y represents C or T, and N represents G, A, T, or C. They were subjected to the PCR thermal cycle 94° C. 1 min.→(25 cycles at 94° C. 1 min.→50° C 1 min.→70° C. 1 min.)→4° C. 1 min. The amplified mixture was analyzed by 0.8% agarose gel electrophoresis. A 400 bp fragment was excised from the gel and purified by means of DNA extracting kit (Takara Co.), and then DNA base sequence of the fragment was determined by means of DNA sequencer (373 A type, Applied Biosystems Co.) with DNA sequence kit (ABI PRISM™ Dye Terminator Cycle Sequence Ready Reaction Kit with Amplitaq$^R$ DNA polymerase, FS) according to the supplier's instruction. As a result, as base sequence corresponding to nucleotides 514 to 905 of Seq. ID No. 1 was obtained. The amino acid sequence translated from the base sequence had regions "VGDFLLG" (SEQ. ID No. 9) and "EGEVLQL" (SEQ ID No. 10) which were characteristic to the synthetic enzyme of prenyl diphosphate having long prenyl chain. Accordingly, we confirmed the obtained gene was a part of decaprenyl diphosphate synthase gene.

Example 2

Agrobacterium sp. KNK712 chromosomal DNA (0.25 µg) was subjected to PCR amplification with primers NQE-11 (having the sequence of 5'-AAGTCCACCGCCCGCACGATCT-3' (SEQ ID No. 5)) and NQE-12 (having the sequence of 5'-CCGAGGTTCATGCCGTAGGATTTT (SEQ ID No. 6)). The PCR was carried out at 94° C. 1 min.→(25 cycles at 94° C. 1 min.→50° C. 1 min.→70° C. 1 min.)→4° C. 1 min. The amplified mixture was separated by 0.8% agarose gel electrophoresis, and about 320 bp fragment was excised from the gel and then the fragment was purified by means of DNA extracting kit (Takara Co.). 25 ng of the obtained DNA fragment was labeled with [α-32P]dCTP by means of Megaprime™ DNA labeling system (Amersham Co.).

Example 3

Agrobacterium sp. KNK712 chromosomal DNA was digested with restriction enzyme EcoRI, Sac I, Not I and Xho I, and separated by 0.8% agarose gel electrophoresis. Then, the gel was denatured by means of alkaline solution (0.5M NaOH, 1.5M NaCl) and neutralized (0.5M Tris.HCl (pH 7.5)). Highbond N+ filter (Amersham Co.) was placed on the gel and the DNA bands on the gel were Southern transferred to the filter with 10×SSC. The obtained filter was dried and fixed at 80° C. for 2 hours, and then, the filter was prehybridized at 60° C., for 4 hours in the prehybridizing solution (15 ml of 20×SSC (3M NaCl, 0.3M trisodium citrate dihydrate, pH 7.0), 5 ml of 10% SDS (sodium dodecyl sulfate), 5 ml of 50×Denhardt's solution (10 g/l FicoIR Type 400, (Pharmacia), 10 g/l of polyvinylpyrrolidone and 10 g/l bovine serum albumin (Fraction V, Sigma)), 0.5 ml of 10 mg/ml salmon sperm DNA (denatured by heating at 95° C. for 5 minutes and quenched on ice) and 24.5 ml of water).

The labeled probes were heated at 95° C. for 5 min and quenched on ice, and were added into the prehybridizing solution containing the prehybridized filter. Hybridization was carried out at 60° C. for 22 hours. The hybridized filter was washed two times at room temperature with 5×SSC supplemented with 0.5% SDS, and then with 1×SSC supplemented with 0.1% SDS while the temperature was gradually increased from 60° C. to 75° C. The filter was dried and exposed by adhering to the X-ray film, and then black bands were developed.

As a result, the probes were strongly hybridized with EcoRI fragment of about 2.7 kb, Sac I fragment of about 4.7 kb, Not I fragment of about 8.3 kb, and Xho I fragment of about 4.7 kb.

Example 4

A chromosomal DNA of Agrobacterium sp. KNK 712 was cut with EcoRI restriction enzyme, separated by 0.8% agarose gel electrophoresis, then a DNA fragment of approx. 7 kb was excised and purified to give the DNA fragment for cloning. The obtained DNA fragment was inserted into the λ-ZAP II phage kit (Stratagene Co.) at EcoRI site and packaged using in vitro packaging kit (Amersham Co.). Then, E-coli XL 1-Blue MRF' was infected with the phage. The infected cells were plated onto NZY plate culture medium (5 g/l NaCl, 2 g/l MgSO4/7H2O, 5 g/l yeast extract, 10 g/l NZ amine, 18 g/l agar (pH 7.5) together with NZY soft agar medium (same as NZY plate culture medium except for the amount of agar is 8 g/l) and cultured to develop plaques. The plaques were transferred on to the Highbond N+ filter (Amersham Co.). The filter was denatured with an alkaline solution (0.5M NaOH, 1.5M NaCl), neutralized (0.5M Tris.HCl(pH 7.5), 1.5M NaCl), dried and fixed at 80° C. for 2 hours.

Twenty-four filters obtained as above were prehybridized and then hybridized with labeled probes according to the similar procedure of Example 3, and the obtained filters were washed. After being dried, the filters were exposed to X-ray by adhering to the X-ray films. Plaques of the phages corresponding to the black spots developed were isolated. The isolated phages were infected into E-coli according to the above-described method. The obtained plaques were blotted onto the filter and again hybridized to confirm. Twelve strains of the phage were selected.

PCR was carried out using suspension of the respective phages and the aforementioned NQE-11 and NQE-12. 320 bp DNA fragments were found in eight strains of them. Phagemids were prepared with two strains of the 8 using λ-ZAP II Phage Kit according to the supplier's instruction.

Example 5

Using thus obtained two phagemid DNA's, DNA base sequence of decaprenyl diphosphate synthase gene was determined according to the process similar to example 1. Among the inserted DNAs, a DNA base sequence fragment of about 1.6 kb were determined. The obtained sequence is shown in the sequence listings as Seq. ID No. 1. An amino acid sequence deduced from the base sequence is shown as Seq. ID No. 2.

The obtained sequences were compared with those of decaprenyl diphosphate synthase derived from *Gluconobacter suboxydans* (Japanese Patent Application Laid Open H10-57072) and found that they showed about 47% of amino acid sequence homology and about 60% of DNA sequence homology. The results are shown in FIGS. 3, 4 and 5. The sequences were also compared with decaprenyl diphosphate synthase derived from *Schizosaccaromyces pombe* and found that they showed about 30% amino acid and 46% DNA homologies.

Example 6

Figure 1:
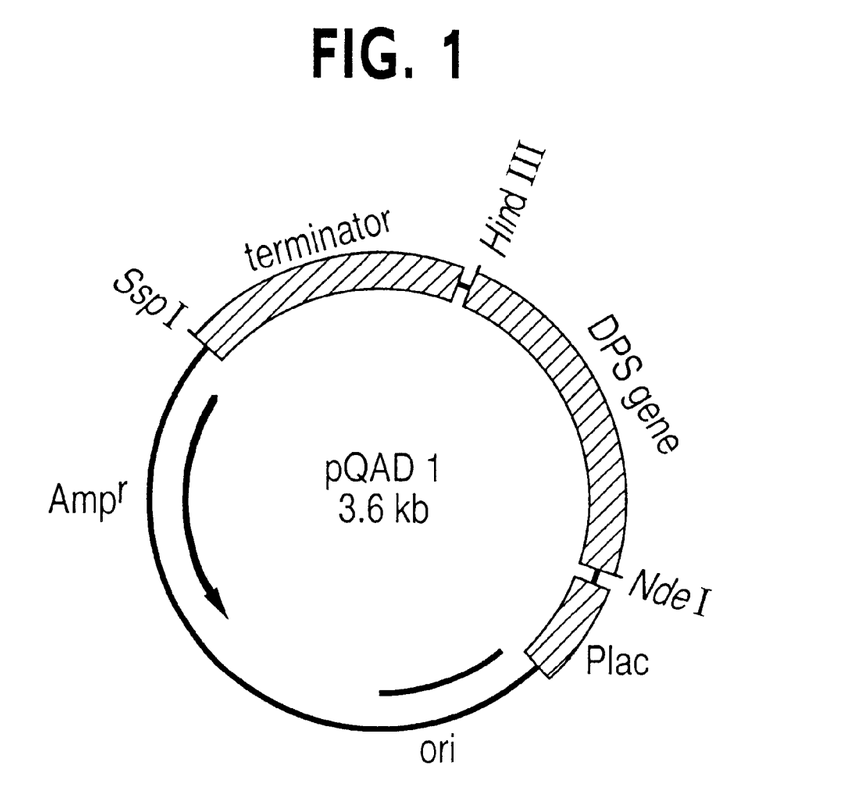
FIG. 1 shows a restriction map of plasmid pQAD1 which contains decaprenyl diphosphate synthase gene.

In order to excise the coding region for decaprenyl diphosphate synthase from the above prepared phagemid, PCR was carried out using synthetic DNA primers NQE-22 (having the sequence of 5'-AGTCAAGCTTCAGCTCACCCGGTCGATC-3' (SEQ ID No. 7)) and NQE-23 (having the sequence of 5'-AGCTCATATGATACCGCTGGAAGACAGC-3' (SEQ ID No. 8)) according to the same procedure as example 3. The obtained fragment was cut with NdeI and Hind III restriction enzymes and the obtained fragment was transferred into the expression vector pUCNT (WO94/03613) to give expression vector pQAD1 for the decaprenyl diphosphate. The restriction map of pQAD1 is shown in FIG. 1. In this figure, DPS represents the coding region of the decaprenyl diphosphate synthase.

Example 7

Thus prepared expression vector for decaprenyl diphosphate synthase was added to *E-coli* HB101, the cells were shaken over night in 10 ml LB medium at 37° C. and then, collected (3000 rpm, 20 min.).

Figure 2:
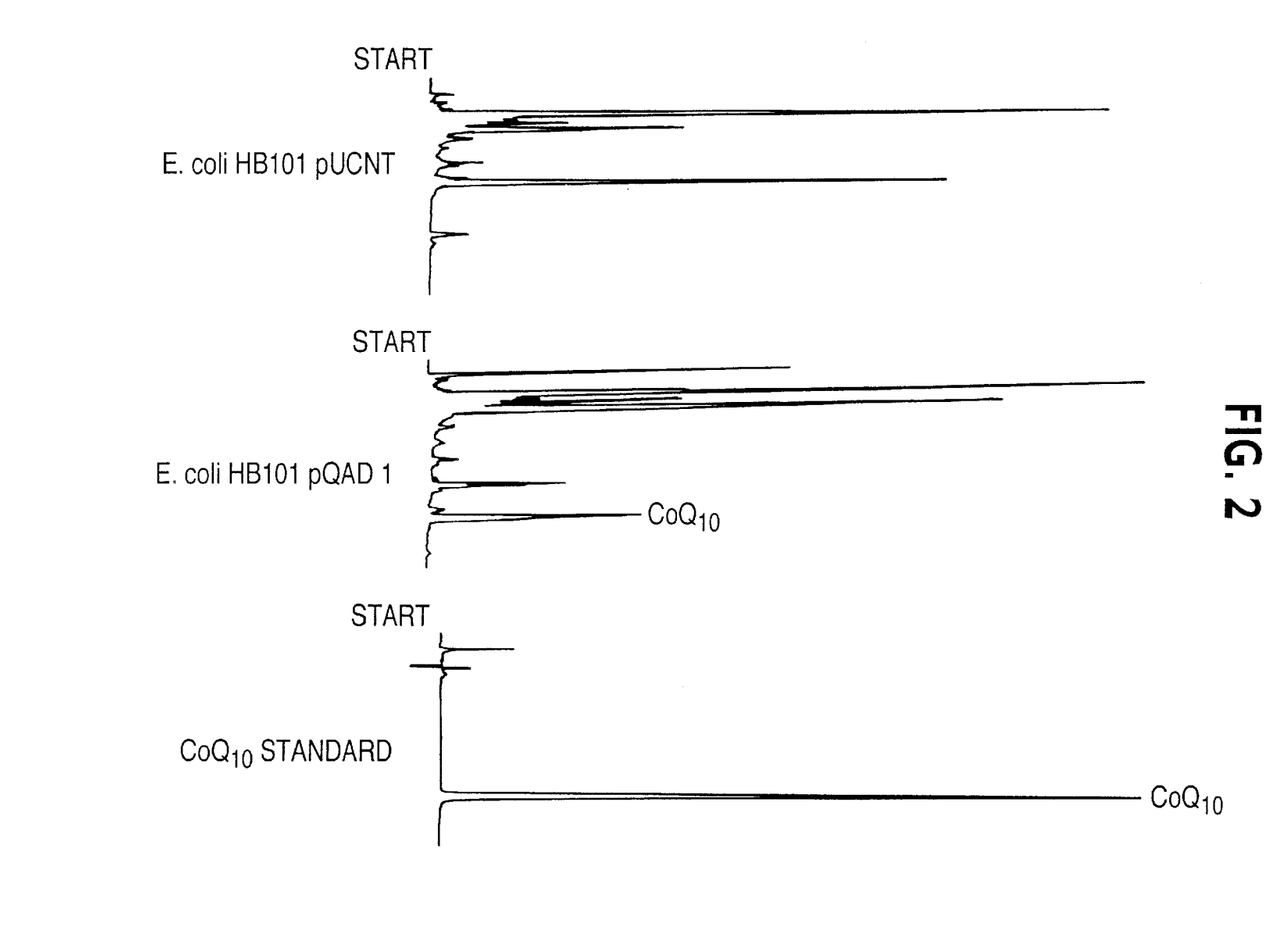
FIG. 2 shows a chart of high-speed liquid chromatography detecting coenzyme $Q_{10}$ produced by recombinant *E-coli* comprising decaprenyl diphosphate synthase gene.

The collected cells were suspended into 1 ml of 3% aqueous sulfuric acid, heated to 120° C. for 30 minutes, added with 2 ml of 14% aqueous sodium hydrate and heated to 120° C. for additional 15 minutes. Thus treated mixture was extracted by adding 3 ml of hexane/isopropanol (10:2) and centrifuged. 1.5 ml of the organic solvent phase was separated and evaporated to dryness under reduced pressure. The residue was dissolved in 0.5 ml ethanol and 20 μl of the solution was analyzed with high speed liquid chromatography system (LC-10A; Shimadz Co.). For elution, reverse phased column (YMC-pack ODS-A, 250×4.6 mm, S-5 μm, 120A) was used and ethanol/methanol (2:1) was used as a mobile phase solvent. The produced coenzyme $Q_{10}$ was monitored by absorbance at 275 nm wavelength. Results are shown in FIG. 2. As is apparent from FIG. 2, the recombinant *Escherichia coli* obtained by introducing and expressing decaprenyl diphosphate synthase gene produce coenzyme $Q_{10}$, which is not produced by wild type strain.

The obtained recombinant *E-coli* strain, *Escherichia coli* HB101 pQAD1 was deposited in the National Institute of Bioscience and Human-Technology, Agency of Industrial Science and Technology, Ministry of International Trade and Industry on Oct. 1, 1996, (Accession No. FERM BP-6538.)

In the present invention, a gene coding for decaprenyl diphosphate synthase, the key enzyme in the coenzyme $Q_{10}$ biosynthetic system, was isolated from the bacterium belonging to the family Rhizobiaceae and the nucleotide sequence was determined. In addition, the inventors succeeded in introducing the obtained gene into *Escherichia coli* and expressing the same. By using the gene and the process of the present invention, coenzyme $Q_{10}$, which can be used for manufacturing pharmaceutical compositions and the like, can be prepared effectively.

*Escherichia coli* HB101 pQAD1 was deposited in the National Institute of Bioscience and Human-Technology, Agency of Industrial Science and Technology, Ministry of International Trade and Industry on Oct. 1, 1996. The accession No. FERM BP-6538 was assigned.

What is claimed is:

1. An isolated polynucleotide which encodes a protein having decaprenyl diphosphate synthase activity, said polynucleotide comprising (a) the nucleotide sequence as set forth in SEQ ID No. 1, (b) a nucleotide sequence which hybridizes under stringent hybridization conditions to the nucleotide sequence as set forth in SEQ ID No. 1, said stringent hybridization conditions comprising hybridizing and washing in 1×SSC at about 60° C. or (c) a nucleotide sequence which encodes the amino acid sequence as set forth in SEQ ID No. 2.

2. The isolated polynucleotide according to claim 1 which comprises the nucleotide sequence as set forth in SEQ ID No. 1.

3. The isolated polynucleotide according to claim 1, which encodes a decaprenyl diphosphate synthase comprising the amino acid sequence as set forth in SEQ ID No. 2.

4. A process for producing coenzyme $Q_{10}$ comprising transforming a host microorganism with the polynucleotide according to claim 1, culturing the transformed host microorganism, and isolating coenzyme $Q_{10}$.

5. The process according to claim 2, wherein the host microorganism is *Escherichia coli.*

6. The process according to claim 2, wherein the transformed host microorganism is *Escherichia coli* HB101 pQAD1 (FERM BP-6538).

7. An expression vector comprising the polynucleotide according to claim 1.

8. An expression vector pQAD1, obtained by transferring the polynucleotide according to claim 1 into an expression vector pUCNT.

9. A host microorganism transformed with the polynucleotide according to claim 1.

10. The microorganism according to claim 9, which is an *Escherichia coli.*

11. The microorganism according to claim 10, wherein the *Escherichia coli* is *Escherichia coli* HB 101 pQAD1 (FERM BP-6538).

12. A host microorganism transformed with the expression vector according to claim 7.

13. The microorganism according to claim 12, which is an *Escherichia coli.*

14. The microorganism according to claim 13, wherein the *Escherichia coli* is *Escherichia coli* HB 101 pQAD1 (FERM BP-6538).

15. An isolated protein which is coded by the polynucleotide according to claim 1 and has a decaprenyl diphosphate synthase activity.

16. An isolated protein which comprises the amino acid sequence of SEQ ID No. 2 and has a decaprenyl diphosphate synthase activity.

* * * * *

UNITED STATES PATENT AND TRADEMARK OFFICE
CERTIFICATE OF CORRECTION

| | | |
|---|---|---|
| PATENT NO. | : 6,461,842 B1 | |
| APPLICATION NO. | : 09/673018 | |
| DATED | : October 8, 2002 | |
| INVENTOR(S) | : Hideyuki Matsuda et al. | |

It is certified that error appears in the above-identified patent and that said Letters Patent is hereby corrected as shown below:

Column 15, Claim 5, line 1, please change "2" to -- 4 --.

Column 15, Claim 6, line 1, please change "2" to -- 4 --.

Signed and Sealed this

Twenty-second Day of May, 2007

JON W. DUDAS
*Director of the United States Patent and Trademark Office*

SEQUENCE LISTING

<160> NUMBER OF SEQ ID NOS: 10

<210> SEQ ID NO 1
<211> LENGTH: 1586
<212> TYPE: DNA
<213> ORGANISM: Agrobacterium sp.
<220> FEATURE:
<221> NAME/KEY: CDS
<222> LOCATION: (238)..(1242)

<400> SEQUENCE: 1

```
ggacccctcc agaatgctca tgccctgatc ggcgatcagg ctgttaatac cggcatcctt      60
catcaggctg tcggcaaaag agagcagaac gacgtcgttg gtgcggatca attccttcat    120
ccagcggttt ttcctgtcct atttcagcaa gcgggacaat tcgcctcttg ccgcacgtgc    180 cccccttcc tattgtcgaa agcgacaatg aaaacaggag tcccggtgtt gggcgta        237 gtg ata ccg ctg gaa gac agc aaa aac aaa cag gcg tcc gtc aag ccg      285
Val Ile Pro Leu Glu Asp Ser Lys Asn Lys Gln Ala Ser Val Lys Pro
  1               5                  10                  15 ctc gtt gac ctg aca tct ccc gac atg gaa cgc gtc aac cag ctc atc      333
Leu Val Asp Leu Thr Ser Pro Asp Met Glu Arg Val Asn Gln Leu Ile
               20                  25                  30 ctg tcg agg gcc ggc tcc gac gtc cag atg att ccc gag gtt gcc aac      381
Leu Ser Arg Ala Gly Ser Asp Val Gln Met Ile Pro Glu Val Ala Asn
           35                  40                  45 cac ctg atc tcg tcg ggt ggc aag cgc ctg cga ccg atg ctg acg ctc      429
His Leu Ile Ser Ser Gly Gly Lys Arg Leu Arg Pro Met Leu Thr Leu
       50                  55                  60 gcc tcc gcc gcc atg ttc ggc tac gag ggc gac gct cac gtc aag ctc      477
Ala Ser Ala Ala Met Phe Gly Tyr Glu Gly Asp Ala His Val Lys Leu
   65                  70                  75                  80 gcc acc agc gtc gag ttc atg cac acg gca aca ctg ctg cat gac gat      525
Ala Thr Ser Val Glu Phe Met His Thr Ala Thr Leu Leu His Asp Asp
                       85                  90                  95 gtc gtg gac gaa agc gat ctg cgc cgc ggc aag tcc acc gcc cgc acg      573
Val Val Asp Glu Ser Asp Leu Arg Arg Gly Lys Ser Thr Ala Arg Thr
                   100                 105                 110 atc tgg ggc aac cag gca agc gtt ctt gtc ggc gat ttc ctc ctc ggc      621
Ile Trp Gly Asn Gln Ala Ser Val Leu Val Gly Asp Phe Leu Leu Gly
               115                 120                 125 cag gcc ttc cgc atg atg gta gat gtc ggc tcg ctc gat gcg ctc gac      669
Gln Ala Phe Arg Met Met Val Asp Val Gly Ser Leu Asp Ala Leu Asp
           130                 135                 140 gtg ctt tcg acc gca gcc tcg gtg atc gcc gag ggc gaa gtg ctg cag      717
Val Leu Ser Thr Ala Ala Ser Val Ile Ala Glu Gly Glu Val Leu Gln
145                 150                 155                 160 ctt tcg gtc gcc aag aac atg gag acg acc gaa gac gac tat ctc cag      765
Leu Ser Val Ala Lys Asn Met Glu Thr Thr Glu Asp Asp Tyr Leu Gln
                165                 170                 175 gtc atc cgc gcc aag acc gca gcg ctc ttt gct gcg gcc gcc gaa gtc      813
Val Ile Arg Ala Lys Thr Ala Ala Leu Phe Ala Ala Ala Ala Glu Val
            180                 185                 190 ggc ccg atc gtc gcc cag acc agc aag tcc gac cgc aat gcg cta aaa      861
```

```
Gly Pro Ile Val Ala Gln Thr Ser Lys Ser Asp Arg Asn Ala Leu Lys
            195                 200                 205 tcc tac ggc atg aac ctc ggc ctc gcc ttc cag ctc gtc gat gac gtg      909
Ser Tyr Gly Met Asn Leu Gly Leu Ala Phe Gln Leu Val Asp Asp Val
        210                 215                 220 ctt gac tat ggc ggc tcg gcc agc gac ctc ggc aag aat gtc ggc gac      957
Leu Asp Tyr Gly Gly Ser Ala Ser Asp Leu Gly Lys Asn Val Gly Asp
225                 230                 235                 240 gat ttc cgt gaa ggc aag atc acc ctg ccg gtg atc ctg tcc tat cgc     1005
Asp Phe Arg Glu Gly Lys Ile Thr Leu Pro Val Ile Leu Ser Tyr Arg
                245                 250                 255 cgc ggt acg ccg gag gat cgc gcc ttc tgg cgt gag gcg atc gaa ggc     1053
Arg Gly Thr Pro Glu Asp Arg Ala Phe Trp Arg Glu Ala Ile Glu Gly
        260                 265                 270 ggc gac agc agc gat tcg aac ctc gaa agg gca ctc ggc ctg atc aaa     1101
Gly Asp Ser Ser Asp Ser Asn Leu Glu Arg Ala Leu Gly Leu Ile Lys
275                 280                 285 cgt tat ggc ggc ttg agc gat acc atc gcc cgc gcc cag cac tac ggc     1149
Arg Tyr Gly Gly Leu Ser Asp Thr Ile Ala Arg Ala Gln His Tyr Gly
                290                 295                 300 acg att gca cgc gat gcc ttg gca ccg ctc ccg gtt tcg ccg tgg aaa     1197
Thr Ile Ala Arg Asp Ala Leu Ala Pro Leu Pro Val Ser Pro Trp Lys
305                 310                 315                 320 tcg gca ctg gtc gag gtc atc gac ttc tgc atc gac cgg gtg agc         1242
Ser Ala Leu Val Glu Val Ile Asp Phe Cys Ile Asp Arg Val Ser
                325                 330                 335 tgacgcgacc ttcggccgaa ccgggacata caagaggaat tcttgccgc gttgcgccaa    1302 aaaagccatt ctgttcctca agagttgtgc cgggcaacac gtggccgatt ccagaacaac   1362
cctcagtcgt gcgcaaggcc gagagatcgg caatgaaagg tttgatatgc ggcaaaagac   1422
gatcctccgc cttctgagcg gcgctgcact gatggctctt gccaccgtcg gcggcagcta   1482
ccaggctttc gccgaggaaa aggccgccgt cgaggagacc gagcctttcg acatcacgac   1542
cgtcaacacc tttgccggcg cattcctttg ccgcccgcac ggct                   1586

<210> SEQ ID NO 2
<211> LENGTH: 335
<212> TYPE: PRT
<213> ORGANISM: Agrobacterium sp.

<400> SEQUENCE: 2

Val Ile Pro Leu Glu Asp Ser Lys Asn Lys Gln Ala Ser Val Lys Pro
  1               5                  10                  15

Leu Val Asp Leu Thr Ser Pro Asp Met Glu Arg Val Asn Gln Leu Ile
            20                  25                  30

Leu Ser Arg Ala Gly Ser Asp Val Gln Met Ile Pro Glu Val Ala Asn
        35                  40                  45

His Leu Ile Ser Ser Gly Gly Lys Arg Leu Arg Pro Met Leu Thr Leu
    50                  55                  60

Ala Ser Ala Ala Met Phe Gly Tyr Glu Gly Asp Ala His Val Lys Leu
65                  70                  75                  80

Ala Thr Ser Val Glu Phe Met His Thr Ala Thr Leu Leu His Asp Asp
                85                  90                  95

Val Val Asp Glu Ser Asp Leu Arg Arg Gly Lys Ser Thr Ala Arg Thr
            100                 105                 110

Ile Trp Gly Asn Gln Ala Ser Val Leu Val Gly Asp Phe Leu Leu Gly
        115                 120                 125
```

```
Gln Ala Phe Arg Met Met Val Asp Val Gly Ser Leu Asp Ala Leu Asp
    130                 135                 140
Val Leu Ser Thr Ala Ala Ser Val Ile Ala Glu Gly Glu Val Leu Gln
145                 150                 155                 160
Leu Ser Val Ala Lys Asn Met Glu Thr Thr Glu Asp Asp Tyr Leu Gln
                165                 170                 175
Val Ile Arg Ala Lys Thr Ala Ala Leu Phe Ala Ala Ala Glu Val
            180                 185                 190
Gly Pro Ile Val Ala Gln Thr Ser Lys Ser Asp Arg Asn Ala Leu Lys
            195                 200                 205
Ser Tyr Gly Met Asn Leu Gly Leu Ala Phe Gln Leu Val Asp Asp Val
        210                 215                 220
Leu Asp Tyr Gly Gly Ser Ala Ser Asp Leu Gly Lys Asn Val Gly Asp
225                 230                 235                 240
Asp Phe Arg Glu Gly Lys Ile Thr Leu Pro Val Ile Leu Ser Tyr Arg
                245                 250                 255
Arg Gly Thr Pro Glu Asp Arg Ala Phe Trp Arg Glu Ala Ile Glu Gly
            260                 265                 270
Gly Asp Ser Ser Asp Ser Asn Leu Glu Arg Ala Leu Gly Leu Ile Lys
        275                 280                 285
Arg Tyr Gly Gly Leu Ser Asp Thr Ile Ala Arg Ala Gln His Tyr Gly
    290                 295                 300
Thr Ile Ala Arg Asp Ala Leu Ala Pro Leu Pro Val Ser Pro Trp Lys
305                 310                 315                 320
Ser Ala Leu Val Glu Val Ile Asp Phe Cys Ile Asp Arg Val Ser
                325                 330                 335

<210> SEQ ID NO 3
<211> LENGTH: 24
<212> TYPE: DNA
<213> ORGANISM: Agrobacterium sp.
<220> FEATURE:
<221> NAME/KEY: base
<222> LOCATION: (10)
<223> OTHER INFORMATION: n = g, a, t or c
<221> NAME/KEY: base
<222> LOCATION: (11)
<223> OTHER INFORMATION: y = c or t
<221> NAME/KEY: base
<222> LOCATION: (13)
<223> OTHER INFORMATION: n = g, a, t or c
<221> NAME/KEY: base
<222> LOCATION: (16)
<223> OTHER INFORMATION: y = c or t
<221> NAME/KEY: base
<222> LOCATION: (19)
<223> OTHER INFORMATION: y = c or t
<221> NAME/KEY: base
<222> LOCATION: (22)
<223> OTHER INFORMATION: y = c or t
<223> OTHER INFORMATION: Description of Artificial Sequence: DNA Primers

<400> SEQUENCE: 3
aaggatcctn ytncaygayg aygt                                       24

<210> SEQ ID NO 4
<211> LENGTH: 25
<212> TYPE: DNA
<213> ORGANISM: Agrobacterium sp.
<220> FEATURE:
<221> NAME/KEY: base
<222> LOCATION: (11)
<223> OTHER INFORMATION: r = a or g
<221> NAME/KEY: base
```

```
<222> LOCATION: (14)
<223> OTHER INFORMATION: n = g, a, t or c
<221> NAME/KEY: base
<222> LOCATION: (17)
<223> OTHER INFORMATION: n = g, a, t or c
<221> NAME/KEY: base
<222> LOCATION: (19)
<223> OTHER INFORMATION: r = a or g
<221> NAME/KEY: base
<222> LOCATION: (20)
<223> OTHER INFORMATION: y = c or t
<221> NAME/KEY: base
<222> LOCATION: (23)
<223> OTHER INFORMATION: r = a or g
<223> OTHER INFORMATION: Description of Artificial Sequence: DNA Primers

<400> SEQUENCE: 4
aaggatcctc rtcnacnary tgraa                                          25

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: DNA Primers

<400> SEQUENCE: 5
aagtccaccg cccgcacgat ct                                             22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: DNA Primers

<400> SEQUENCE: 6
ccgaggttca tgccgtagga tttt                                           24

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: DNA Primers

<400> SEQUENCE: 7
agtcaagctt cagctcaccc ggtcgatc                                       28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: DNA Primers

<400> SEQUENCE: 8
agctcatatg ataccgctgg aagacagc                                       28

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Peptide
      Fragment

<400> SEQUENCE: 9
```

```
Val Gly Asp Phe Leu Leu Gly
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Peptide
      Fragment

<400> SEQUENCE: 10

Glu Gly Glu Val Leu Gln Leu
  1               5
```